(12) United States Patent
Berggren et al.

(10) Patent No.: US 6,436,699 B1
(45) Date of Patent: Aug. 20, 2002

(54) CAPACITY AFFINITY SENSOR

(75) Inventors: Christine Berggren; Gillis Johansson, both of Lund (SE)

(73) Assignee: AB Sangtec Medical, Bromma (SE)

( * ) Notice: Subject to any disclaimer, the term of this patent is extended or adjusted under 35 U.S.C. 154(b) by 0 days.

(21) Appl. No.: 09/508,782

(22) PCT Filed: Sep. 2, 1998

(86) PCT No.: PCT/SE98/01562

§ 371 (c)(1), (2), (4) Date: Jun. 15, 2000

(87) PCT Pub. No.: WO99/14596

PCT Pub. Date: Mar. 25, 1999

(30) Foreign Application Priority Data

Sep. 15, 1997 (SE) ............................................. 9703314

(51) Int. Cl.$^7$ ........................... C12M 1/34; C12M 1/00; C12M 1/42; C07K 1/00; C07H 21/02
(52) U.S. Cl. ............................... 435/287.2; 435/283.1; 435/285.2; 435/287.1; 530/350; 536/23.1
(58) Field of Search ......................... 435/6, 7.1, 7.94, 435/91.1, 183, 283.1, 285.2, 287.1, 287.2; 436/94, 501; 536/23.1, 23.2, 24.3; 530/300, 350, 387.1; 424/130.1, 178.1, 184.1, 94.1, 198.1

(56) References Cited

U.S. PATENT DOCUMENTS 4,824,532 A * 4/1989 Moingeon et al. ............ 204/72
5,834,224 A * 11/1998 Ruger et al. .................. 435/14

OTHER PUBLICATIONS

Taira et al., Electrode modification by long–chain, dialkyl disulfide reagent having terminal dinitrophenyl group and its application to impedimetric immunosensors. Anal. Sci., 9, 199–206, 1993.*

Duan et al., Separation–free sandwich enzyme immunoaaaays using microporous gold electrodes and self–assembled monolayer/immobilized capture antibodies. Anal. Chem., 66, 1369–1377, May 1994.*

Livache et al., Preparation of a DNA matrix via an electrochemically directed copolmerization of pyrrole and oligonucleotides bearing a pyrrole group. Nucleic Acids Res., 22, 2915–2921, 1994.*

Bryant et al., Surface raman scattering of self–assembled monolayers formed from 1–alkanethiols at Ag. J. Am. Chem. Soc., 113, 3629–3637, May 1991.*

* cited by examiner

Primary Examiner—Ethan C. Whisenant
Assistant Examiner—Frank Lu
(74) Attorney, Agent, or Firm—SEED Intellectual Property Law Group PLLC

(57) ABSTRACT

This invention describes a capacity affinity sensor based on self-assembled monolayers on an electrode with immobilized recognition elements available to analyte in the surrounding solution. Additional insulation is provided by auxiliary self-assembled molecules. The sensor has exceptional sensitivity and wide operating range due to these parts of the invention. It is versatile because different kinds of recognition elements can be immobilized directly on the surface of the measuring electrode. The electrode then becomes selective to those molecules in the solution, the analytes, that show affinity to the recognition element on the surface. Compared to capacitive sensors described before those described here shows at least a 1000-fold better sensitivity because of the properties of the layer binding the recognition element.

18 Claims, 12 Drawing Sheets

CAPACITY AFFINITY SENSOR

Detecting interactions between molecules forms the basis of many analytical methods. The interaction can be detected and quantified through a number of schemes, e.g. precipitation, separation or through different marker molecules or reactions. Such an example is the development of immunoassays during the last three decades, which has revolutionized determination of drugs and hormones in clinical and pharmaceutical chemistry as well as contaminants in the environmental area. Almost all immunomethods require labels attached either to the antibody or the antigen. Another example is the binding between a DNA-probe and its complementary DNA-strand or DNA-fraction. A number of receptors or the complementary molecule can be studied using the same approach.

There are a number of disadvantages associated with labels. It they are radioactive the work has to be carried out under strict safety regime and handling of waste is costly. The use of enzymes as labels requires an additional time-consuming incubation step. Common for all labels are that they require a synthetic coupling to either an antigen or an antibody or generally to the recognition element or the analyte. A big label may change the affinity between the molecules which is of particular concern when an assay is performed by. competition between an analyte from the sample and an added labeled molecule. Many affinity interactions cannot be studied because of this. Recognition of DNA-binding through the use of electrochemical intercalators shows low sensitivity. Many attempts have therefore been made to detect the binding itself by potentiometric [Taylor, R. F.; Marenchic, I. G.; Spencer, R. H. *Anal. Chim. Acta* 1991, 249, 67–70], piezoelectric [Roederer, J. E.; Bastiaans, G. J. *Anal. Chem.* 1983, 55, 2333– 2336], or optical measurements [Löfås, S. *Pure Appl. Chem.* 1995, 67, 829–834].

Attempts have previously been made to use capacitance measurements for detecting molecular interactions without the use of labels. A molecule with affinity for the analyte should be immobilized on a conducting electrode surface so that it can interact with the analyte in solution in such a way that the interaction causes a change in capacitance. This principle has been used in immunochemistry, by immobilization to oxide surfaces [Bataillard, P.; Gardies, F.; Jaffrezic-Renault, N.; Martelet, C.; Colin, B.; Mandrand, B. *Anal. Chem.* 1988, 60, 2374–2379] or for recognition of DNA-sequences [Souteyrand, E.; Martin, J. R.; Cloarec, J. P.; Lawrence, M. *Eurosensors X, The 10th European Conference on Solid-State Transducers*, 1996, Leuven, Belgium].

Self-assembled monolayers of thiols, sulfides and disulfides on gold electrodes have been widely studied and long-chain alkanethiols are known to form insulating well-organized structures on gold substrates [Porter, M. D.; Bright, T. B.; Allara, D. L.; Chidsey, C. E. D. *J. Am. Chem. Soc* 1987, 109, 3559–3568]. The binding formed between the sulphur atom and gold is very strong and the formed self-assembled monolayers (SAM's) are stable in air, water and organic solvents at room temperature [Bain, C. D.; Troughton, E. B.; Tao, Y.-T.; Evall, J.; Whitesides, G. M.; Nuzzo, R. G. *J. Am. Chem. Soc.* 1989, 111, 321–335]. It has been suggested that microcontact printing [Mrksich, M.; Whitesides, G. M. *Tibtech* 1995, 13, 228–235] and photolithography [Bhatia, S. K.; Hickman, J. J.; Ligler, F. S. *J. Am. Chem. Soc.* 1992, 114, 4432–4433] can be used to pattern surfaces with functionalized self-assembled monolayers for biosensor production with low cost for a diversity of applications, but until now it has not been possible to produce direct affinity sensors with high sensitivity.

Terrettaz et al, *Langmuir* 1993, 9, 1361–1369, discloses a sensor, e.g. for assaying cholera toxin, where the ganglioside GM1 has been bound to a SAM layer. The detection limit for capacitance measurements using the sensor is somewhere within the range from $10^{-6}$ to $10^{-9}$ M. The article states that capacitance measurements are unsuitable for assaying cholera toxin because the capacitance changes were too small, and hence, the sensitivity is too low.

Self-assembled monolayers of thiols on gold, with antigenic terminating groups have been reported before, but they had coverages of only 14, 19 or 31% for different electrodes [Taira, H.; Nakano, K.; Maeda, M.; Takagi, M. *Anal. Sci.* 1993, 9, 199–206]. The lowest measured value in the article was at an antibody concentration of 10 ng/ml, which can be compared to 1 pg/ml of antigen measured with our invention (See Example 1). The higher sensitivity obtained with our electrode can be explained by that the gold surface is first covered with a self-assembled monolayer of a thiol, sulphide or disulphide giving a high coverage of the surface, therafter the recognition element is immobilized on the surface and as the last step the surface is plugged with another thiol. The saturation seems to occur at similar concentrations in the two cases if the larger bulk of the antibody compared to the antigen is taken into account. This comparison thus supports the arguments given above that a dense layer is of great importance for a high sensitivity.

DNA-probes have been immobilized e. g to $SiO_2$ and a sensitivity of 10 ng/ml was obtained [Souteyrand, E.; Martin, J. R.; Cloarec, J. P.; Lawrence, M. *Eurosensors X, The 10th European Conference on Solid-State Transducers*, 1996, Leuven, Belgium].

A peptide bound to an alkylthiol was also immobilized as a self-assembled layer on gold, but the antibody concentration was in this case in the mg/ml range making it a less succesful sensor [Rickert, J.; Wolfgang, G.; Beck, W.; Jung, G.; Heiduschka, P. *Biosens. Bioelectron.* 1996, 11, 757–768].

One of these previous approaches are illustrated in the patent EP 244326. The recognition element is bound to an insulating layer on top of a conducting substrate, the insulating layer typically being an oxide. The oxide layer has to be thick, typically 70 nm on silicon, in order to be stable and sufficiently insulating, resulting in a low sensitivity. It is difficult to obtain good surface coverage on oxides and the recognition elements are not well ordered.

Rojas, M.; Königer, R.; Stoddart, F.; Kaifer, A.; *J. Am. Chem. Soc.* 1995, 117, 336–343 discloses an assay method for determining ferrocene in a sample using cyclodextrin. All hydroxy groups of cyclodextin are substituted by thiol groups, and the modified cyclodextrins are chemically adsorbed to a gold surface. Empty spaces on the gold surface between the adsorbed modified cyclodextrin molecules are filled with adsorbed pentanethiols. The lowest ferrocene concentration determined is 5 $\mu$M.

There is always a need for improvements of analysis techniques. Especially when assaying biochemical compounds it is often necessary to be able to determine concentrations below 1 ng/ml.

SUMMARY OF THE INVENTION

It has now turned out that unexpectedly good capacity affinity sensors, suitable for determining the presence of a certain compound of interest by capacitance measurements using an electrode which can be produced by a method comprising the steps of:

a) providing a piece, of a noble metal where said piece optionally can be a rod or, alternatively a piece of insulating material such as glass, silica or quartz, on which a noble metal is sputtred or printed;

b) providing a first SAM-forming molecule comprising a coupling group and/or an affinity group specifically binding said compound of interest;

c) contacting the piece in step a) with the first SAM-forming molecule in step b), thereby obtaining a self-assembling monolayer on said noble metal surface;

d) in case the first SAM-forming molecule does not comprise an affinity group, contacting said self-assembling monolayer on said noble metal piece with an affinity molecule specifically binding said compound of interest, thereby coupling the affinity molecule to the self-assembling monolayer; and e) contacting the piece obtained in step c) or d) with a second SAM-forming molecule, thereby obtaining a noble metal surface that is at least 90%, preferably at least 97% covered with a self-assembling monolayer.

DETAILED DESCRIPTION OF THE INVENTION

The detection limits reported in this invention are at least three orders of magnitude better than those reported previously for capacitive immunosensors and a comparison is therefore necessary in order to explain why this invention succeeds so exceptionally well. The insights behind this invention are that the recognition layer must be thin, well-ordered and it must cover at least 90%, preferably at least 95%, more preferably at least 97%, and most preferably at least 99% of the sensor surface. In a subsequent step, any free spots between the recognition elements are "plugged", i.e. covered with a second self-assembling monolayer-forming molecule, e.g. an alkanethiol comprising 3–25 carbon atoms preferably in a straight chain, after obtaining a self-assembling monolayer comprising affinity groups, thereby increasing the tightness and insulation. A capacitive biosensor is covered by an immobilized layer with the recognition element toward the solution. Electrically it is equivalent to a capacitor between the conducting metal electrode and the conducting solution. Another layer forms when a molecule binds to the recognition element thereby replacing aqueous solution with a non-conducting organic molecule. This is equivalent to the formation of an additional capacitor in series with the first, thereby decreasing the total capacitance.

Any part of the surface that allows the aqueous solution to penetrate below the plane where the recognition takes place will act like a short-circuiting element. The capacitance will therefore increase due to the higher dielectric constant of the penetrating aqueous solution. Oxide layers are not well ordered and it is therefore impossible to form a dense recognition layer. Self-assembled monolayers are much better ordered and a more perfect coverage can therefore be expected in the immobilized layers. Furthermore the self-assembled monolayers are much thinner than the oxide layers, resulting in a larger capacitance in series with the capacitance formed when molecules bind on the surface. This makes it easier to detect changes in the capacitance when an analyte binds to the surface.

This invention describes an capacity affinity sensor based on measurements of the capacitance change at conducting surfaces. The grafted recognition layer should be electrically insulating to prevent interferences from redox couples in the electrolyte solution and high Faradaic background currents. On the other hand, it should be as thin as possible in order to achieve high sensitivity. The use of self-assembled binding to gold or other noble metals gives especially thin and compact layers. The invention also shows how additional insulation can be obtained by plugging with a different type of self-assembling molecule.

Accordingly, the present invention relates to a method for producing a capacity affinity sensor, wherein a piece of a noble metal is covered with a layer of a self-assembling monolayer-forming molecule comprising coupling groups. Affinity molecules are then coupled to these self-assembling monolayer-forming molecules. Subsequently any remaining free spots on the noble metal surface is covered by a second self-assembling monolayer-forming molecule.

In another aspect, the present invention relates to a capacity affinity sensor comprising a noble metal piece substantially completely covered with a self-assembling monolayer comprising first and second self-assembling monolayer-forming molecules, and where affinity molecules that specifically binds to a certain molecule of interest have been coupled to the first self-assembling monolayer-forming molecules.

In yet another aspect, the present invention relates to a method for qualitatively or quantitatively determining the presence of a certain compound of interest. A capacity affinity sensor, comprising a noble metal piece substantially completely covered with a self-assembling monolayer comprising first and second self-assembling monolayer-forming molecules, and where affinity molecules that specifically binds to a certain molecule of interest have been coupled to the first self-assembling monolayer-forming molecules, is contacted with a liquid sample comprising the compound of interest and the sensor's capacitance is determined.

In a further aspect, the present invention relates to using said sensors for analysing certain compounds of interests, such as human chorionic gonadotropin hormone (HCG), interleukin-2, human serum albumin, atrazine or a certain DNA sequence.

Definitions

As disclosed herein, the terms "self-assembled monolayer" and "SAM" are synonyms and relates to the spontaneous adsorption of film components from a solution onto a solid surface making a well-ordered monolayer. Such a layer on gold substrates have previously been described substrates [Porter, M. D.; Bright, T. B.; Allara, D. L.; Chidsey, C. E. D. *J. Am. Chem. Soc* 1987, 109, 3559–3568].

As disclosed herein, the term "noble metal" relates to a metal chosen from the group of gold, silver, copper, platinum and palladium. Gold is preferred.

As disclosed herein, the term "affinity molecule" relates to a molecule which specifically binds to a certain molecule of interest. If the molecule to be determined is an antigen, the affinity molecule might be an antibody, preferably a monoclonal antibody, or an antibody fragment such as a $F(ab')_2$ fragment. If a certain nucleic acid sequence is to be identified, the affinity molecule might be a nucleic acid probe specifically hybridizing to said nucleic acid sequence. The present invention can also be used in relation to affinity-mediating biomolecules in general, for example in situations where certain nucleic acids bind to antigens other than nucleic acids, such as proteins. The skilled person is well aware of how to choose suitable affinity molecules for a certain compound to be determined.

As disclosed herein, the term SAM-forming molecule relates to a molecule having the ability of forming a self-assembling monolayer on a noble metal. A SAM-forming molecule comprises at least one thiol, sulphide or disulphide group and may optionally also comprise an affinity group. Affinity molecules are coupled to small SAM-forming molecules comprising coupling groups in a separate step Examples of such small SAM-forming molecules comprising coupling groups are thioctic acid and cysteamine. This coupling step is carried out after formation of the self-assembling monolayer on the noble metal surface. The skilled person is well aware of how to choose suitable coupling reactions and coupling groups. In the following examples, a self-assembling monolayer consisting of thioctic acid is activated by 1-(3-dimethylaminopropyl)-3-ethyl-carbodiimide. Subsequently, an affinity molecule is coupled to the activated monolayer. However, other similar coupling reactions are described in the literature.

As disclosed herein, the term "plugging" refers to treatment in a solution containing a thiol, sulphide or disulphide after immobilization of the affinity molecule to a self-assembling monolayer on a noble metal surface in order to block any unblocked spots on said surface. As already mentioned, it is necessary that the noble metal surface is as completely covered by a SAM as possible in order to optimize the sensitivity of the sensor. Suitable examples of SAM-molecules that can be used for plugging are thiols comprising 3–25 carbon atoms in a straight satured chain. Such SAM-molecules lack coupling groups. A preferred example is 1-dodecanethiol.

As disclosed herein, SCE stands for the saturated calomel electrode; Potentiostatic perturbation means a fast change in potential; HCG stands for human chorionic gonadotropin; IL-2 stands for interleukin 2 and HSA stands for human serum albumin.

The interactions that can be measured using this capacitance sensor includes antigen-antibody, hapten-antibody, peptide-protein, nucleic acids, lectin-hydrocarbon-containing parts, biotin-streptavidin-avidin, receptors-agonist-antagonist, ligand-cells. Complexes can be one part of the affinity pair, e. g. hapten-antibody binding to immobilized hapten as recognition element. Fragment, e. g. of antibodies can be used instead of the native antibody. Recognition element as used in here constitutes any one of the pairs or complexes mentioned above which is immobilized on the electrode surface. Analyte is the molecule to be determined and is normally the other part than the recognition element in the pairs above.

In this invention a solution containing the molecules, complexes or cells to be determined is allowed to make contact with a surface containing the affinity group, after which the capacitance or impedance change when an interaction takes place is determined . The capacitance change takes place between the solution and a metal surface, consisting of solid metal or metal sputtered or printed on an underlaying non-conducting surface. Faradaic reactions with the metal as well as background currents are blocked by the affinity group on the surface, eventually improved by treatment with auxiliary compounds which improve the insulation. The affinity group is bound to the metal surface, either directly through self-assembly, or by binding it to a self-assembled compound on the electrode. It can also be bound through adsorption, polymerization or coating. Measurements are made using electrochemical perturbations followed by recording of the resulting response. The perturbations used in the examples described below are potentiostatic steps or pulses which give rise to current transients from which the capacitance is evaluated. Perturbations can also be amperometric steps in which case the change in potential is used for capacitance evaluation. Perturbations with sinusoidal or other wave-forms have been reported in the litertature. The sensitivity can be improved by allowing a solution containing a secondary specific ligand to bind to the analyte already on the surface, thereby increasing the size of the bound aggregate and the capacitance change.

The invention will now be described in more detail with reference to the enclosed drawings.

FIG. 1a shows schematically how an antibody can be immobilized to a metal surface. An alkane thiol provides additional insulation. It is also shown how the total capacitance is made up from a series connection of those of the double layer, the antibody and the self-assembled layer.

Figure 11:
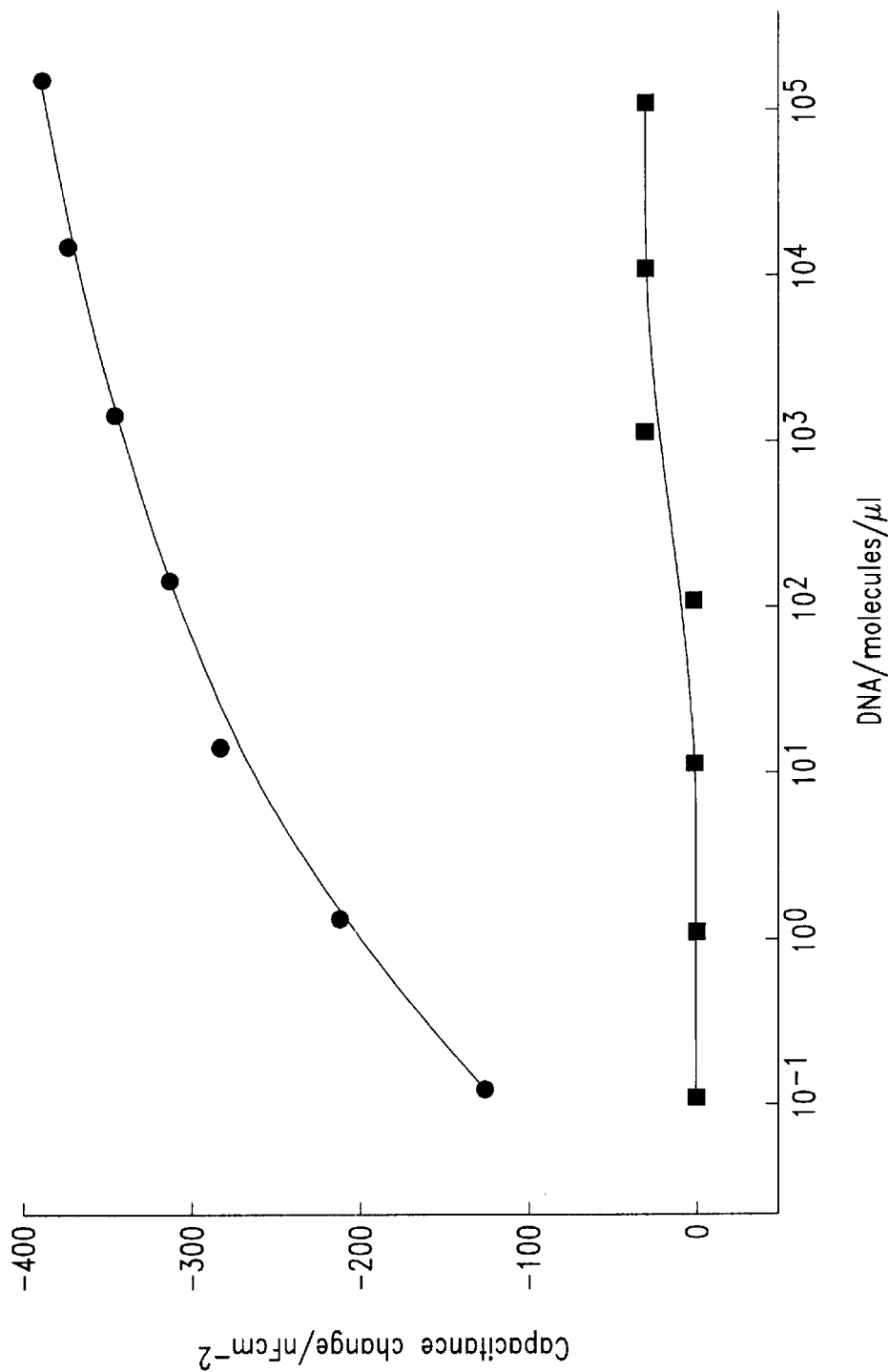

FIG. 11 shows the binding of a cytomegalo virus single stranded 179 base DNA-fragment to an 8 bases long recognition element on the measuring electrode (upper curve) and the non-specific control with a single-stranded 207 base DNA fragment from tyrosinase (lower curve). See example 7 for details.

Figure 12:
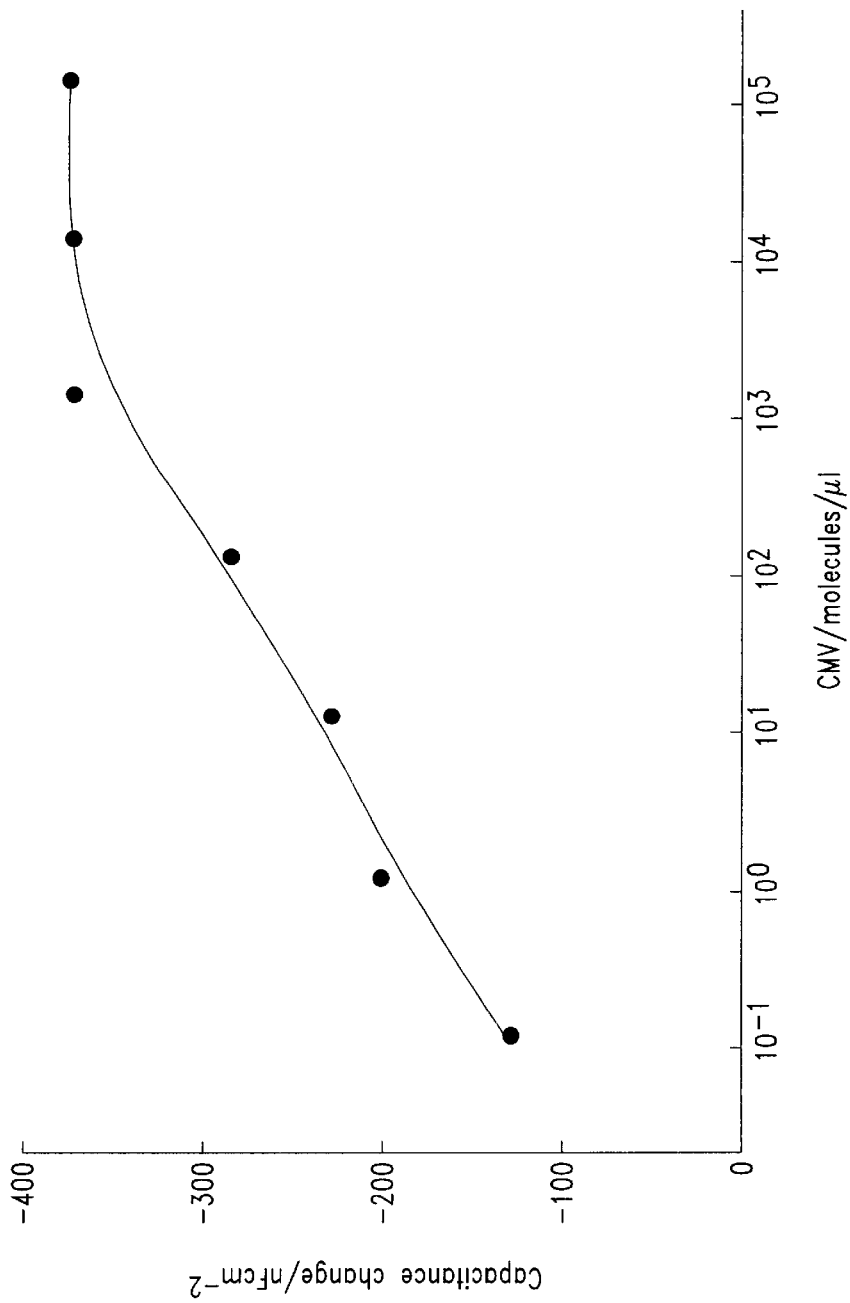

FIG. 12 shows the binding of a cytomegalo virus single stranded 179 base DNA-fragment to a 25 bases long recognition element on the measuring electrode. See example 8 for details.

If a solid measuring metal electrode is used, a gold rod typically 3 mm in diameter, is polished, cleaned and coated through self-assembly with a recognition element or with a compound which can be coupled with a recognition element. A great number of coupling methods are known and may be used as alternatives to those described in the examples. It is also possible to use metal sputtered or printed on glass, quarts, silicon or another insulating materials as disposable electrodes. After cleaning the electrodes are coated in batch and inserted in a quick-connect measuring cell. A number of different recognition elements can be put on the same sputtered electrode if they are separated by insulating parts and connected to the potentiostat with switches which can be controlled by a microprocessor.

The importance of making the recognition layer thin and with a large capacitance is illustrated by FIG. 1 with a coupling chemistry as in Example 1. The inverse total capacitance is the sum of the inverse capacitances of each layer in series, i. e. the thioctic acid layer, the antibody layer and the capacitance between the antibody and solution. If one of these is small compared to the others, it will dominate the total capacitance. Specially if self-assembled parts give rise to a small capacitance, it will dominate over the capacitances in the recognition layer. Changes in the recognition layer will thus have little effect on the total capacitance resulting in a low overall sensitivity of the sensor.

Figure 1A:
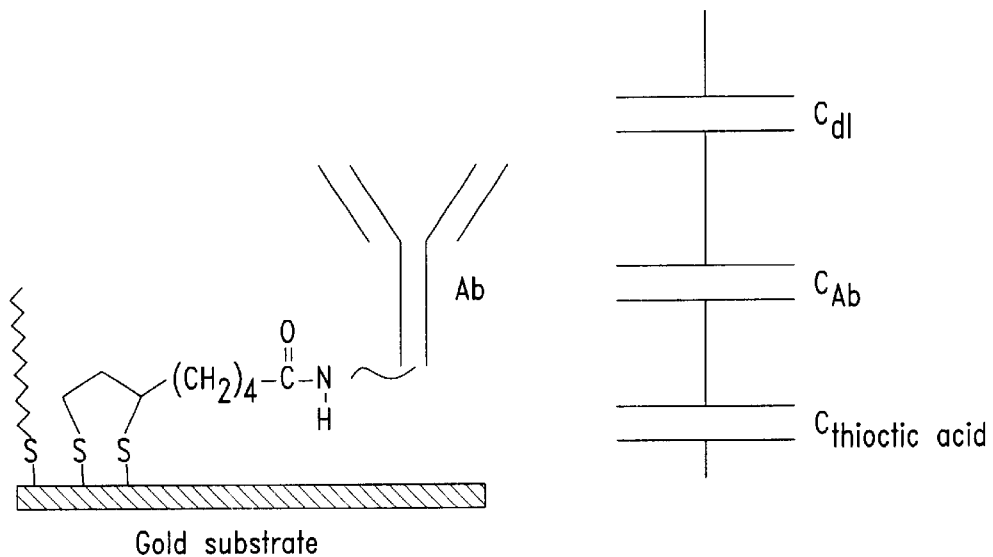
FIG. 1b shows the equivalent circuit used for evaluation of the capacitance.
Figure 2:
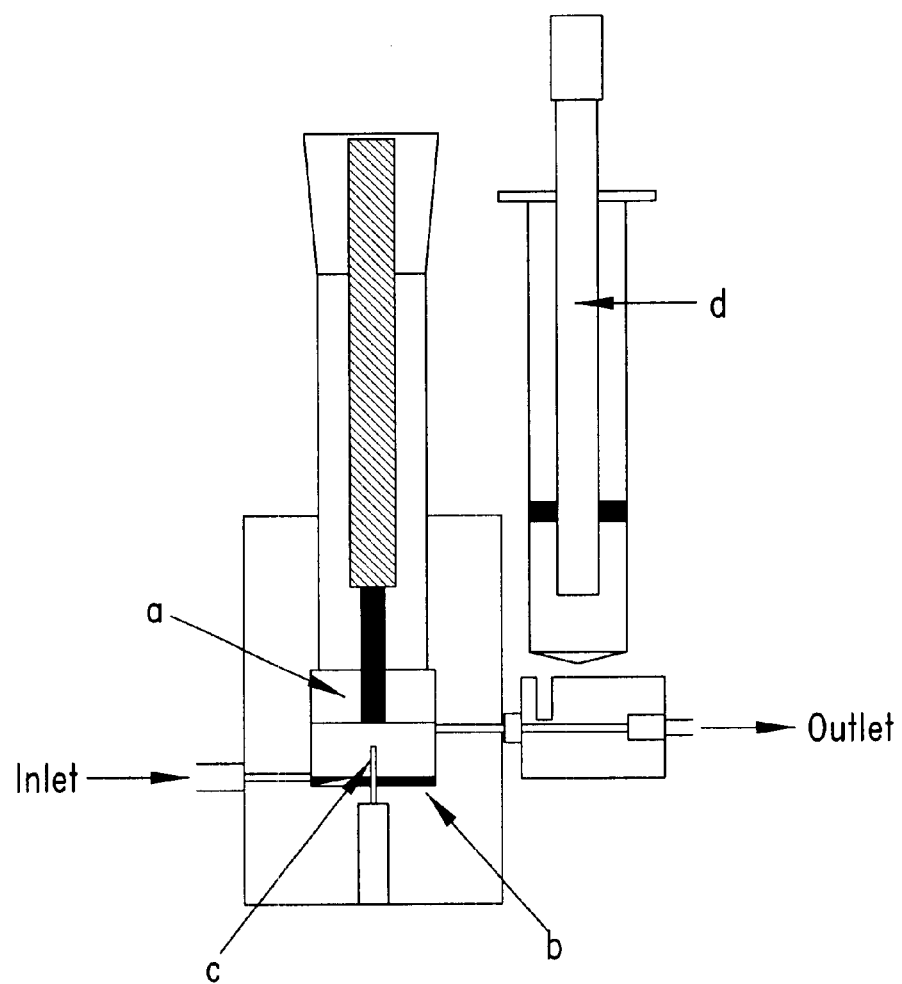
FIG. 2 shows the measuring flow cell, a) measuring electrode, b) auxiliary platinum foil electrode, c) platinum wire reference electrode, d) Ag/AgCl reference electrode.

The electrode is inserted into a cell which may be either of the cuvette type or a flow cell as shown in FIG. 2. The cell must contain an auxiliary electrode, typically a platinum foil which should be placed symmetrically and opposite to the measuring electrode. A reference electrode, typically SCE, is placed in the cell so that the voltage drop between the reference and measuring electrodes due to capacitive or Faradaic currents becomes very small. In some cases the performance may be improved if a very small additional reference electrode is used, see FIG. 1c and the SCE reference is moved away, FIG. 1d. A flow cell gives more precise control over the mass transfer to the measuring electrode and injection of sample and cleaning up is more easily automated. Flow cells with volumes of 2 ml and 10 µl were found to have about the same sensitivity. A flow cell with disposable electrodes made by sputtering gold on silicon also had similar properties.

The electrodes are connected to a fast potentiostat which in turn is controlled from a microprocessor. The potentiostat will keep the measuring electrode at a pre-set value versus the reference. A potentiostatic perturbation is imposed on the measuring electrode. The currents caused by the perturbation voltage are used for evaluation of the capacitance of the measuring electrode.

A known volume of sample is normally mixed with a known volume of a conducting liquid in a cuvette in a batch cell. In the case of a flow cell a known volume is injected into a conducting carrier flow pumped with a known flow rate. The conducting liquids are normally buffers with ionic strengths from a few millimolar and up. The sample can be in a non-conducting medium but a conducting solution must fill the cell when measurements are made.

The invention will now be further described in the following examples. These examples are given for the purpose of illustration and are not intended to limit the scope of the invention.

EXAMPLE 1

Figure 1B:
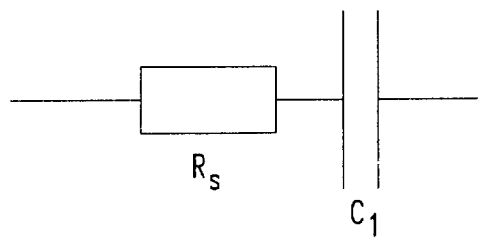

The antibody-covered electrode is schematically shown in FIG. 1a. The electrode was a gold rod (99.99% Aldrich, 3 mm in diameter) cut up into thin sections threaded to stainless steel holders. Prior to immobilization the gold rod was polished with alumina slurries down to 0.04–0.05 µm. After mounting into the Teflon holder the electrode was plasma cleaned for 15 min and immediately placed in a solution of 2% (w/w) D/L-thioctic acid in absolute ethanol. The electrode was taken from the solution after 24 hours, thoroughly rinsed in absolute ethanol and allowed to dry. Thereafter the electrode was put into a solution of 1% (w/w) 1-(3-dimethylaminopropyl)-3-ethyl-carbodiimide hydrochloride in dried acetonitrile for 5 hours. 5 µl (approximately 1 mg/ml) antibody solution was placed on the electrode surface and the coupling procedure was performed at 4° C. for 24 hours. The coupling procedure followed essentially that described by Duan et al [Duan, C.; Meyerhoff, M. E. *Anal. Chem.* 1994, 66, 1369–1377]. A long thiol, 1-dodecanethiol was used to "plug", i.e. block any unblocked spots on the electrode surface.

Capacitance Measurements

The capacitance changes were evaluated from the transient current response obtained when a potentiostatic step was applied to the electrode. An alternative measurement principle relies on the evaluation of the currents at a number of sinusoidal wave frequencies, usually called impedance spectroscopy. The two methods have been compared using the same potentiostat and electrode and found to give almost the same results in terms of equivalent capacitances and resistances. The potentiostatic step method is faster and more convenient and is therefore used here.

The measuring set-up consisted of a three-electrode system, with an extra reference electrode, connected to a fast potentiostat. The potentiostat was connected to a computer (486, 33 MHz) via a Keithley 575 measurement and control system, containing 16-bit A/D and D/A converters. The Keithley system was powered from the computer through a galvanically isolated power line in the box. The potentiostat was powered from the Keithley in order to isolate the analog parts from the noisy digital circuits. The sampling frequency of 50 kHz was determined by an internal clock in the Keithley box. The current values were taken as the mean of ten repeated steps. The rest potential was 0 mV vs. an Ag/AgCl reference electrode. A potential step of 50 mV was applied and the current transient that followed was sampled. An identical current transient but of opposite direction was obtained when the potential was stepped back to the rest value.

Taking the logarithm of the current gives an almost linear curve from which $R_s$ and $C_1$ can be calculated (see FIG. 1b) using the equation:

$$i(t)=u/R_s \exp(-t/R_s{}^*C_1)$$

where i(t) is the current in the circuit as a function of time; u is the applied pulse potential; $R_s$ is the resistance between the gold surface and the reference electrode; t is the time elapsed after the potentiostatic pulse was applied and $C_1$ is the capacitance measured between the gold electrode and the solution. The first ten current values were used for the calculation and a correlation coefficient of better than 0.99 was obtained.

A platinum wire was used as a reference electrode because it can be placed closer to the working electrode than a Luggin capillary of glass without causing any shielding. This will sharpen the current transient and improve the accuracy of the measurements. The platinum reference electrode, though, has no defined potential so its potential was compared to a commercial Ag/AgCl reference electrode, FIG. 1d, just before the potentiostatic pulse was applied.

The carrier solution, 10 mM citrate buffer, pH 7.4 was pumped with a flow rate of approximately 0.5 ml/min through the flow cell. An injector with a loop of 250 µl was connected to the flow system.

Cyclic Voltammetry

Cyclic voltammograms were recorded in a three-electrode system in a batch cell. The working electrode was the unmodified or modified gold rod (3 mm in diameter) in a Teflon holder, the auxiliary electrode was a platinum foil and the reference electrode was a saturated calomel electrode (SCE). 5 mM of a $K_3(Fe(CN)_6)$ solution was used for the measurements. The instrumentation used for cyclic voltammetry was a Princeton Applied 273 A potentiostat controlled by a computer.

Figure 3:
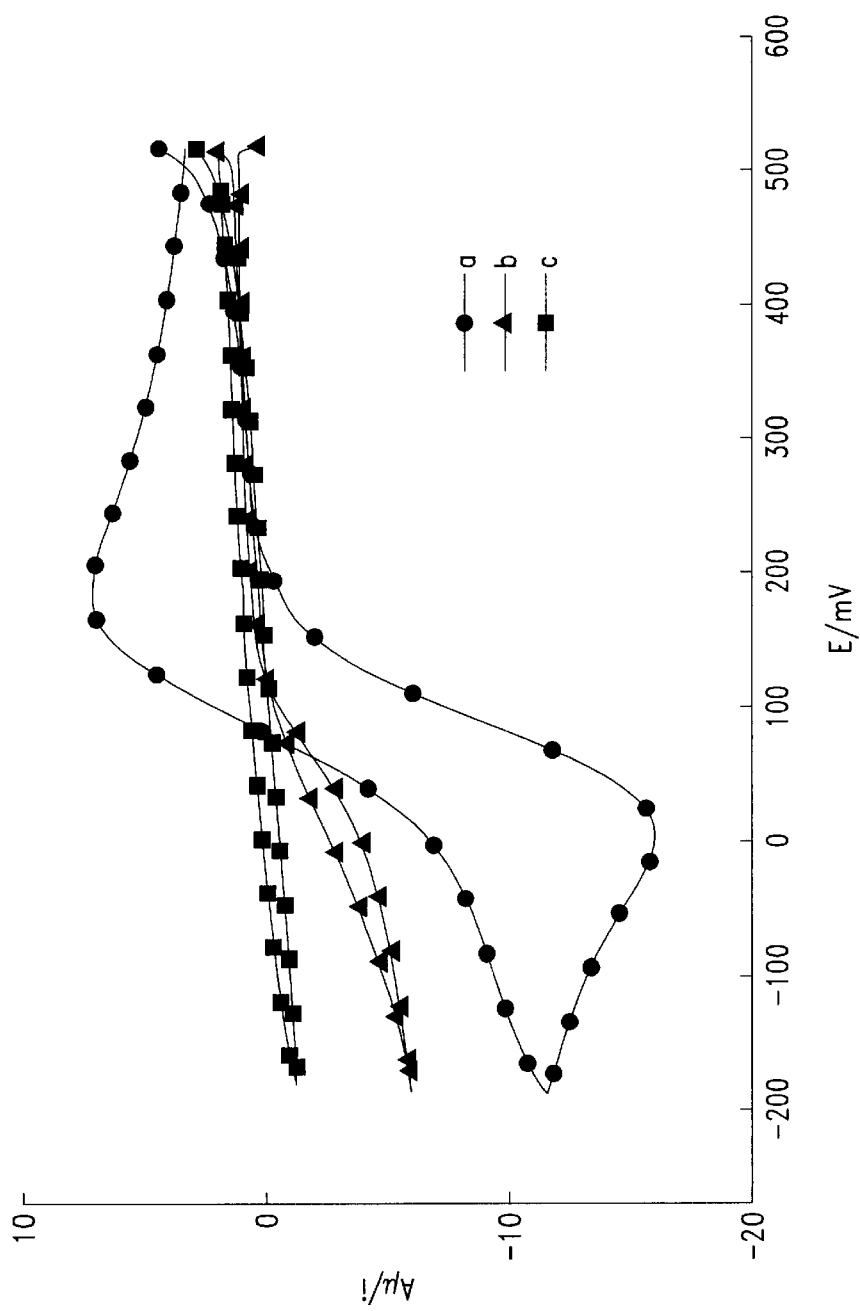
FIG. 3 shows the cyclic voltammetry responses in $Fe(CN)_6^{3-}$ when the measuring electrode was covered with a) thioctic acid, b) thioctic acid and antibody c) thioctic acid, antibody and dodecanethiol. More details are given in example 1.

A gold surface covered with a long chain alkanethiol layer blocks almost all faradaic currents and is highly insulating with an equivalent transfer and dynamic resistance of about 2 000 and 69 $\Omega cm^2$, respectively for a surface covered with butanethiol [Swietlow, A.; Skoog, M.; Johansson, G. *Electroanal.* 1992, 4, 921–928]. A layer of thioctic acid was much less insulating with an equivalent transfer and dynamic resistance of 470 and 40 $\Omega cm^2$, respectively. The permeability of ions through the layer is so high that a redox couple can penetrate it, giving almost the same currents in a cyclic voltammogram as on a bare gold electrode, see FIG. 3, curve a. Immobilization of a monoclonal antibody towards human chorionic hormone (HCG) reduces the penetration of the redox couple, FIG. 3, curve b. Insulation is further improved when the electrode is treated with 1-dodecanethiol as can be seen from the absence of redox peaks for such an electrode, FIG. 3, curve c.

Antigen Detection

When an antigen binds to the antibody immobilized on the electrode, there will be an additional layer decreasing the total $C_1$ further. The binding between the antigen and antibody is therefore detected directly. No label is necessary for the antigen. The physical basis for the response is thought to arise from displacement of the polar water further out from the electrode surface replacing it with a much less polar molecule.

The human chorionic gonadotropin hormone, HCG, was used as model substance. HCG is a glycoprotein with a molecular weight of 30 000 D. The hormone consists of an alpha and a beta chain. The alpha chain is the same as in the thyrotropic hormone, but the beta chains differ in the two hormones. The monoclonal antibody immobilized on the electrode was directed towards the beta chain specific for HCG. Thyrotropic hormone and HCG are known to have a cross-reactivity of less than 0.05% [Sigma Chemical Co., Product specification, C-7659]. The thyrotropic hormone was used as a control for testing the selectivity of the immunosensor.

Figure 4:
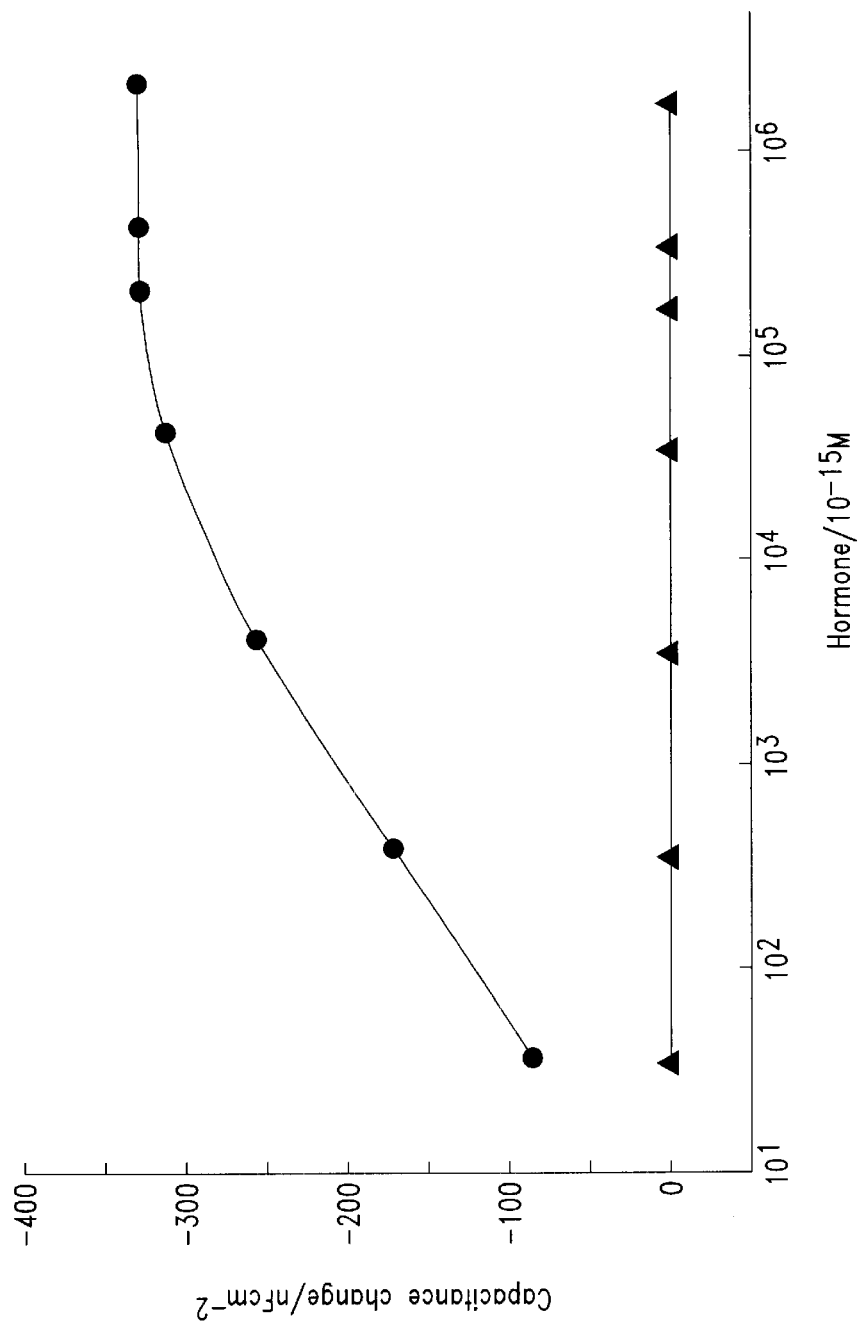
FIG. 4 shows detection of human chorionic gonadotropin hormone (upper curve) and the the lower curve the absence of response to the non-specific thyrotropic hormone (lower curve) as specified in example 1.

Samples with HCG-concentrations as low as 30 $10^{-15}$ M (1 pg/ml) were injected into the flow system. The capacitance was continuously measured and found to decrease after an injection until it reached a stable value, which took approximately 15 minutes in the 2 ml cell with a flow rate of 0.5 ml/min. The change in capacitance vs. the logarithm of the concentration, was found to give a linear relationship up to a concentration of approximately $10^{-11}$ M (0.3 ng/ml) and to reach a saturating value at $10^{-10}$ M, see FIG. 4. The detection limit was around 15 $10^{-15}$ M (0.5 pg/ml) hormone. It was calculated from a comparison between the signal and the irreproducibility of measurements on the antibody surface alone. The irreproducibility corresponds to 15 $nFcm^{-2}$.

As usual in flow injection analysis, the sensitivity and detection limit can be changed by changing the injection volume. A larger sample size will thus decrease the detection limit in proportion.

No cross-reactivity whatsoever was observed on the capacity affinity sensor, when the control antigen, thyrotropic hormone, was injected into the flow system. This suggests that the observed capacitance change is specific and not caused by an unspecific adsorption of protein to the sensor surface. Injection of a serum sample without added HCG produced a 13% increase in the capacitance when the sample entered the cell. The signal returned to the previous value when buffer filled the cell again. The increase in capacity is due to the increased ionic strength of the solution. The experiment thus shows that serum as such does not give rise to any permanent change.

EXAMPLE 2

Capacitance Changes for Antibody Fragments

Figure 5:
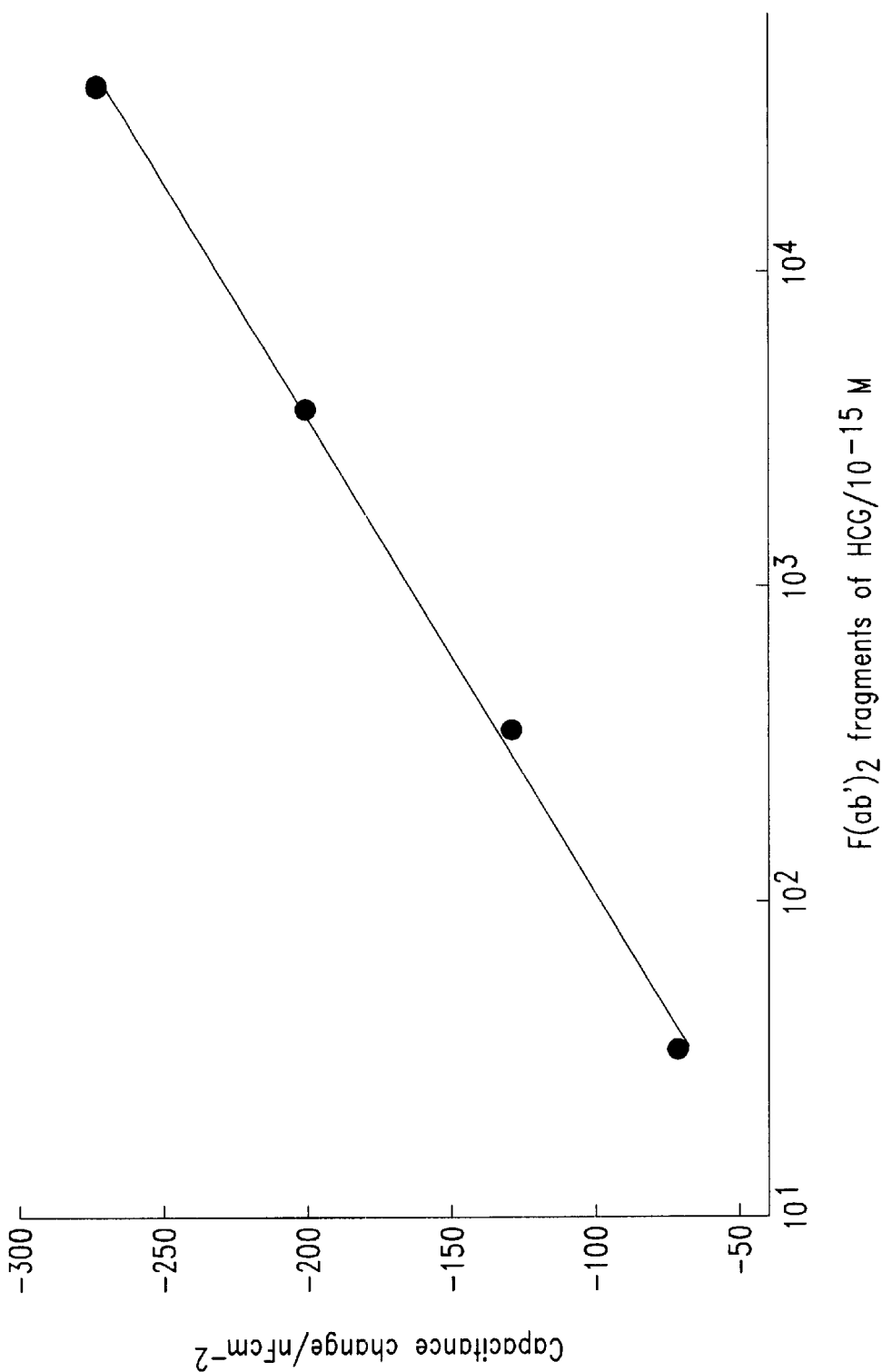
FIG. 5 shows that $F(ab')_2$ fragments can be used as recognition elements for the human chorionic gonadotropin hormone as described in example 2.

To increase the sensitivity of the signal, antibodies against HCG were digested with Ficin to F(ab')$_2$ fragments. The idea is to remove an inactive part of the antibody and to move the binding sites closer to the electrode surface. The fragments were immobilized to the electrode surface in the same way as described above. The analytical properties were similar to those obtained with electrodes covered with the native antibody, as shown in FIG. 5. The capacitance, $C_1$, of the F(ab')$_2$ electrode was 4500 $nFcm^{-2}$ compared to 1400 $nFcm^{-2}$ for an electrode with a native antibody. The resistivities were about 63 $\Omega cm^2$ in both cases. The slopes of the calibration curves were about the same in both cases and an increased sensitivity was not obtained. The increased capacitance will improve the signal-to-noise ratio somewhat.

EXAMPLE 3

The F(ab')$_2$-fragment of HCG was reduced in 0.1 M phosphate buffer, pH 6, containing 0.15 M NaCl, 5 mM EDTA, 4.2 mg/ml 2-mercaptoethylamine during 1.5 h at 37° C. The solution was ultrafiltered on an Amicon dialysis filter, cut-off 10 000 D. The plasma-cleaned gold electrode was dipped into the filtrate at room temperature over night. The electrode was later treated with 1-dodecanethiol.

Figure 6:
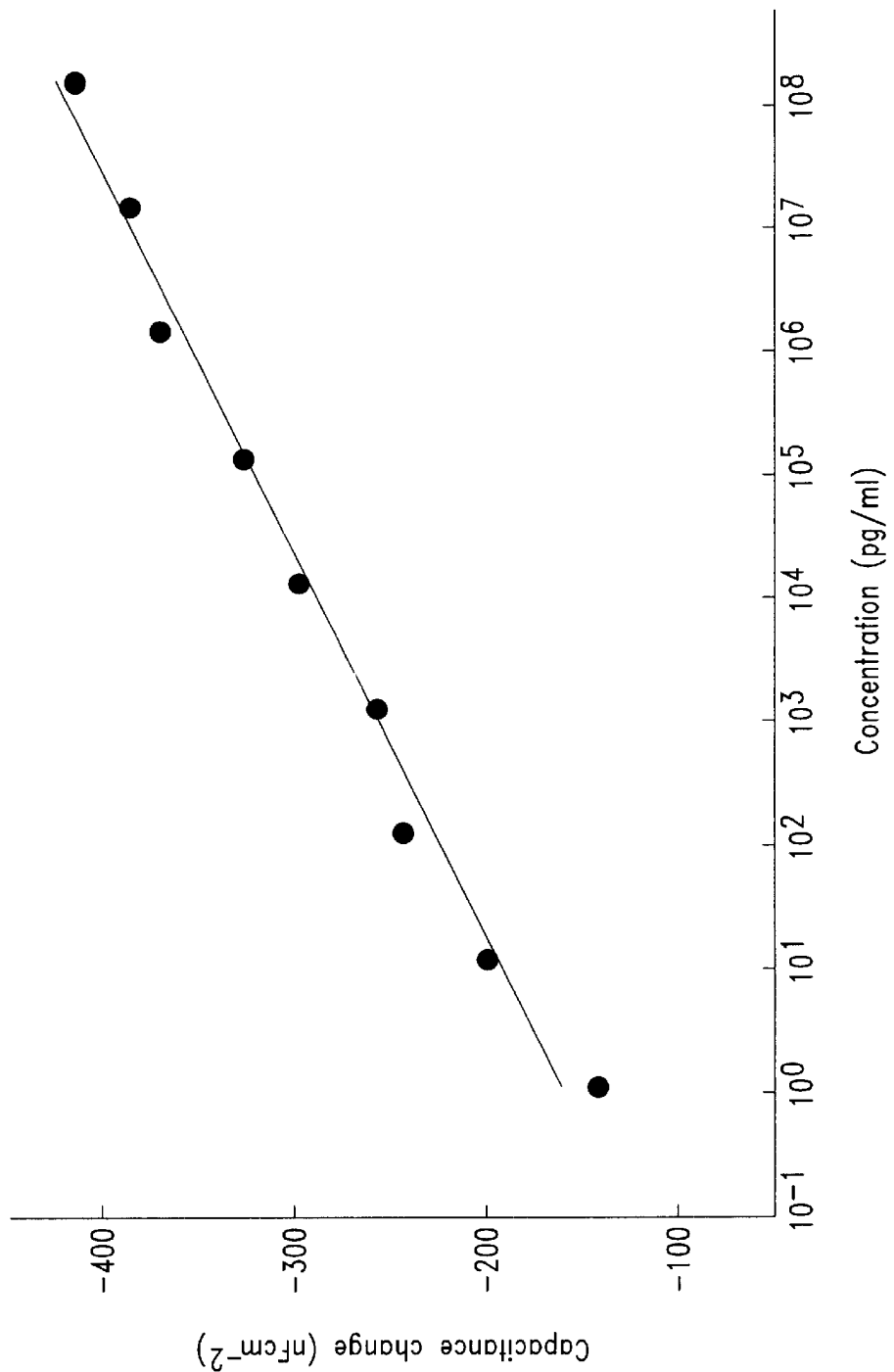
FIG. 6 shows that reduced $F(ab')_2$ fragments can be used as recognition elements for the human chorionic gonadotropin hormone as described in example 3.

The procedure illustrates a direct binding between the sulfur atom of a univalent antibody fragment and the metal. The surface will be even more homogeneous with this procedure and the antibodies' binding part is directed out into solution. The capacitance will be even higher with this treatment and the sensitivity will be higher as shown in FIG. 6.

EXAMPLE 4

Figure 7:
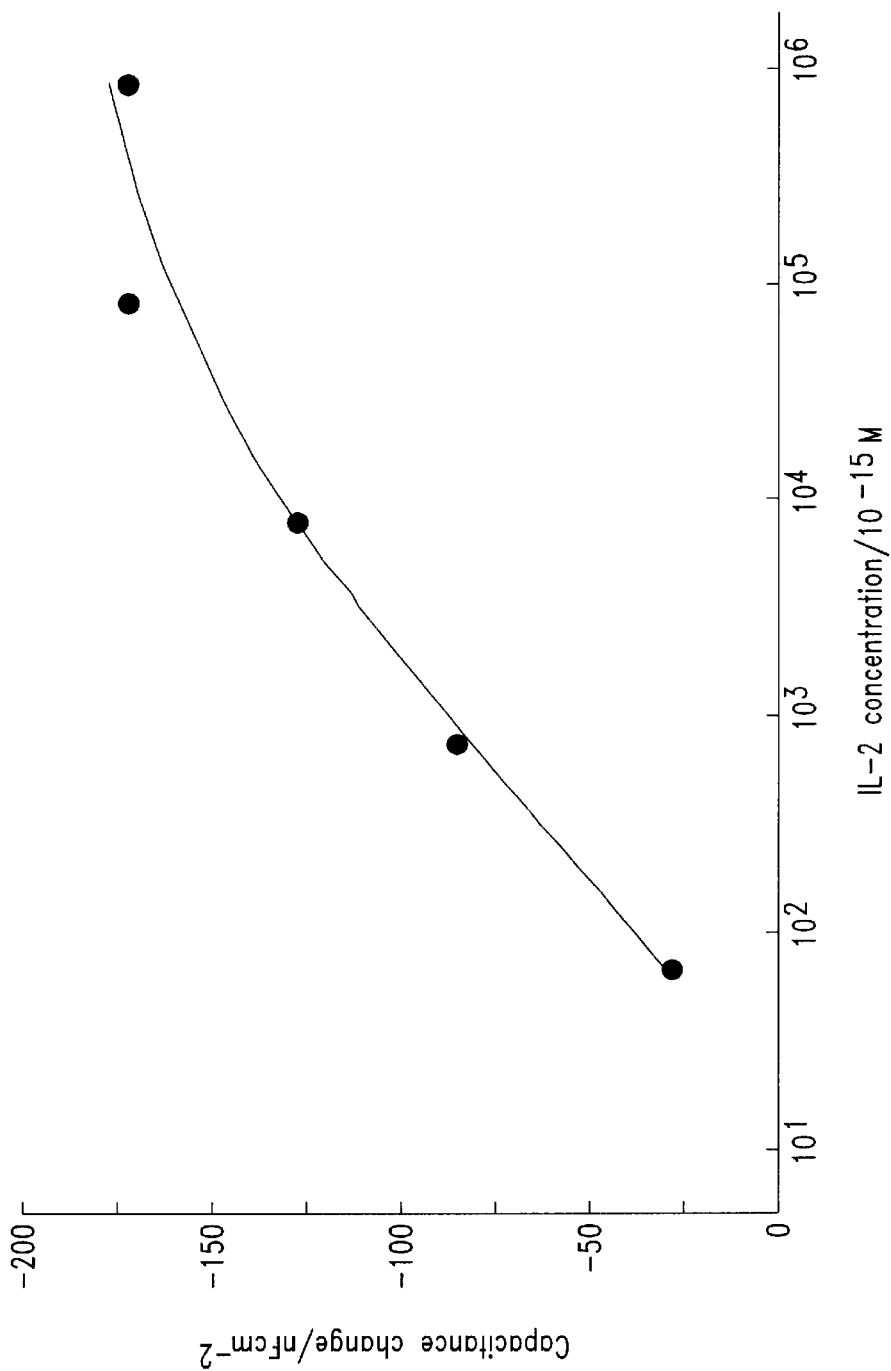
FIG. 7 shows detection of the cytokine Interleukin-2 as mentioned in example 4.

A monoclonal antibody towards Interleukin-2, IL-2 ($M_w$ 15 700 D) was immobilized as described above. The results, see FIG. 7, indicate that the capacitance change was about half as large for IL-2 as for HCG. This can be explained by the larger molecular weight of HCG.

The IL-2 antibody was taken from a commercial sandwich ELISA kit for determination of IL-2 after incubation in micro titer plates with a stated detection limit of 6 pg/ml in medium and 10 pg/ml in serum. The detection limit for the immunosensor is better than 1 pg/ml. Serum samples from apparently healthy donors were all below 31 pg/ml [R & D Systems, Inc., Quantikine, IL-2 manual], i.e. the commercial kit could not reliably measure IL-2-levels in healthy individuals.

EXAMPLE 5

A monoclonal antibody towards human serum albumin, HSA, ($M_w$ 69 000 D) was immobilized on the electrode as described above. The response for HSA was lower than for IL-2, which suggests that more factors than molecular size has to be taken into account. Such factors can be the structure of the antigen, that is if it has a compact or a loose configuration, charges of the antigen and the affinity constant for the antibody-antigen complex. One possibility is that albumin is penetrated by the aqueous phase resulting in an increased polarity of the antigen layer. Another possibility is that the antigen binds in such a way that aqueous solution can penetrate between molecules to some extent. There might be sterical hindrance for two large HSA molecules to bind to an antibody with about the same molecular weight as the two.

Figure 8:
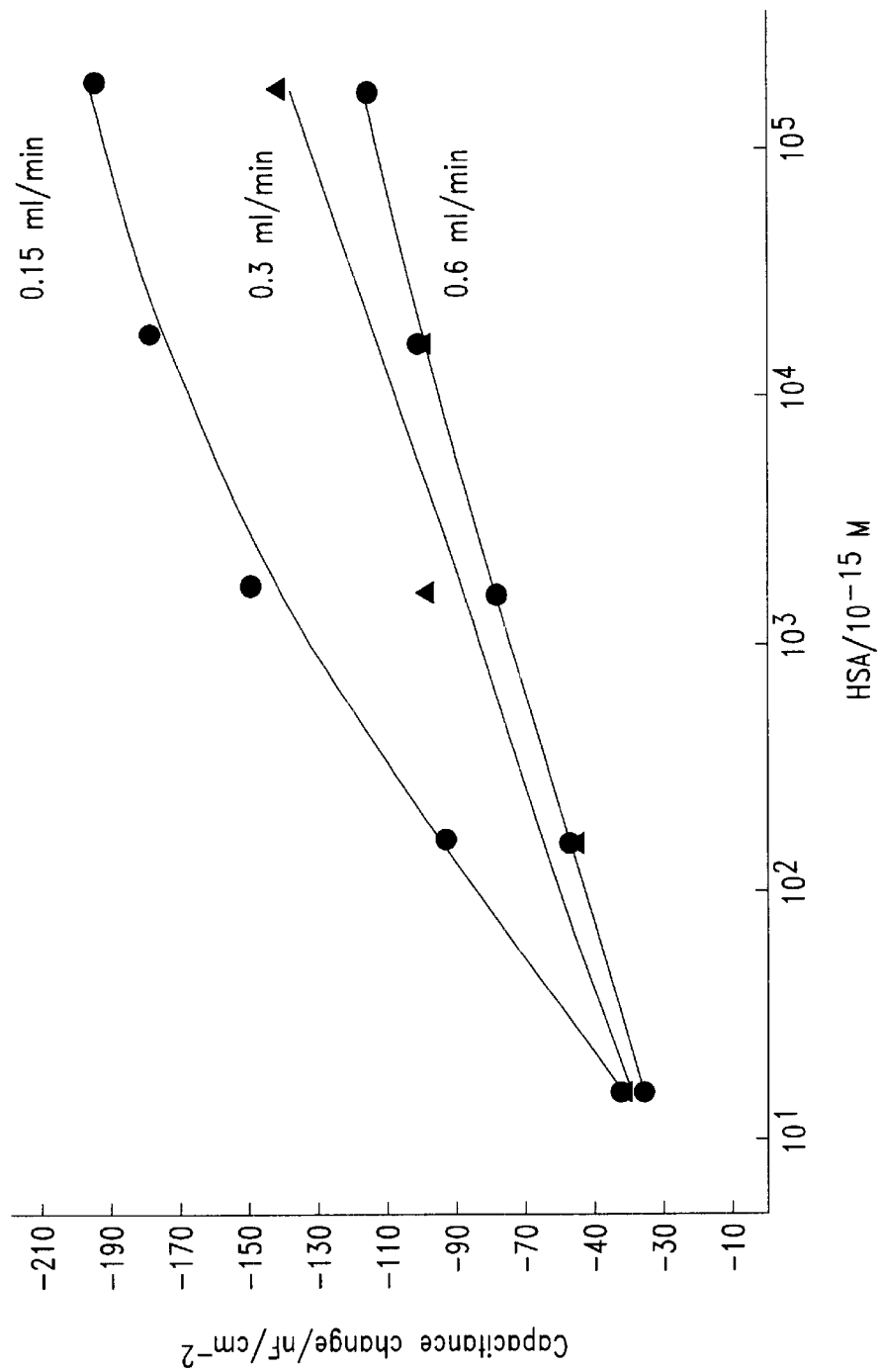
FIG. 8 shows detection of human serum albumin in a flow cell with different flow rates as discussed in example 5.

The capacitance changes obtained for different flow rates were studied for the HSA system and the results are shown in FIG. 8. The capacitance change was found to increase from a flow rate of 0.6 ml/min down to 0.15 ml/min. A longer residence time in the cell will allow more HSA molecules to be transported up to the sensor surface by diffusion and hydrodynamic movements in the solution. An increased sensitivity with decreasing flow rate is therefore generally expected.

A closer look at the curve shapes for HSA at 0.3 and 0.6 ml/min show that they differ from those of the other antigens and from that of HSA at 0.15 ml/min. The lower flow rate gives HSA more time to interact with the antibody and to rearrange itself on the sensor surface. The sensitivity per molecule seems also to increase when the concentration decreases.

EXAMPLE 6

Figure 9:
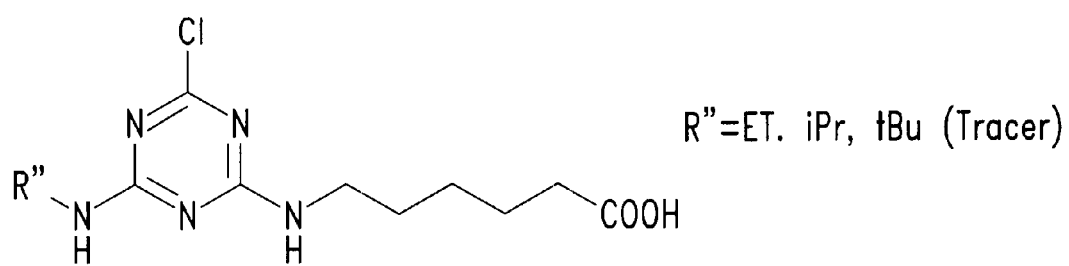
FIG. 9 shows the structure of the modified atrazine discussed in example 6.
Figure 10:
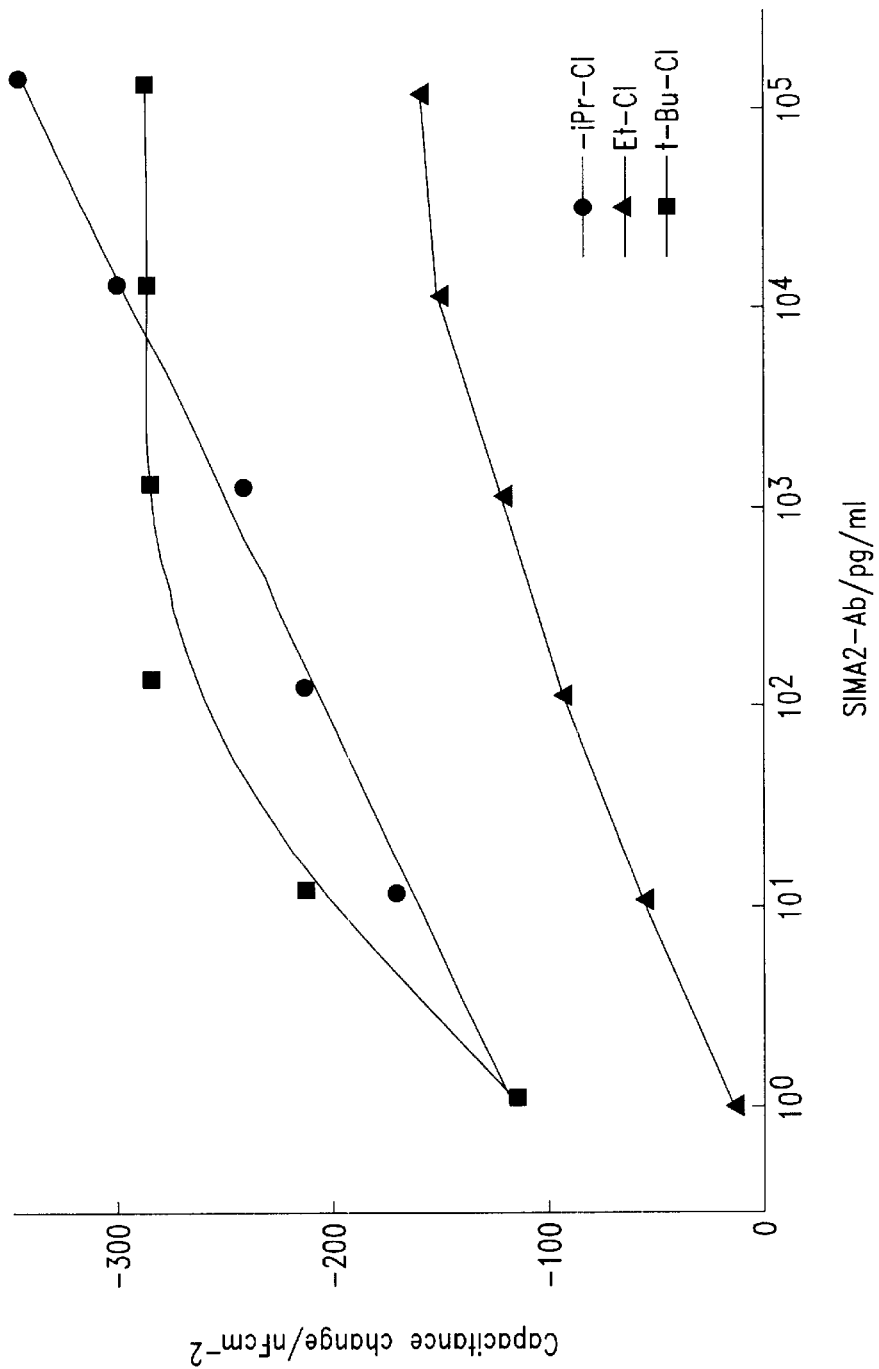
FIG. 10 shows binding of antibodies to atrazines with different side arms, as discussed in example 6.

The herbicide atrazine is a small molecule and the capacitance changes will be small if it binds to an antibody on the measuring electrode. A competitive assay can be made by binding a bulky molecule to the herbicide and to allow this labeled antigen to compete with analyte antigens. A displacement assay can also be performed thus dispensing with the need to use labels. In this assay the antigen was bound to cysteamine self-assembled on gold by coupling to a carboxylic group in the modified antigen with 1-(3-dimethylaminopropyl)-3-ethyl-carbodiimide hydrochloride in dried acetonitrile for 5 hours. Three different side-chains in the antigen were tested, see FIG. 9. The different modified antigens were tested by injecting antibodies, see FIG. 10. It can be seen that the t-butyl derivative binds more efficiently to the antibody than the others. It saturates and reaches a constant level at low antibody concentrations. With an antibody saturated surface, addition of analyte antigen will cause the antibody to be displaced to some degree, proportional to the concentration, to form a soluble complex. The capacitance will increase when the amount of antibody on the surface diminishes. There should be room for the hypervariable region of the antibody to interact with the bound antigen. If the antigens are packed too denseley they may be interspaced with some inactive compounds.

EXAMPLE 7

DNA can be detected by binding a single-stranded DNA-probe to the measuring electrode. The gold surface was treated prior to immobilization as described above. Thereafter it was placed in a thiol solution of 2% (w/w) of cysteamine in ethanol for 16 hours. After reaction the electrode was thoroughly rinsed in ethanol and dried. The coupling of the oligonucleotide to the phosphorylated 5' end was performed in an 0.1 M imidazole buffer, pH 6–7, containing 0.15 M 1-(3-dimethylaminopropyl)-3-ethyl-carbodiimide hydrochloride, at room temperature for 16 hours. After reaction the electrode was rinsed in buffer and placed in the flow-cell.

An oligonucleotide consisting of 8 bases (SEQ.ID.NO.1) displaying the base sequence of the cytomegalo virus showed capacitance changes when an 179 long single-stranded DNA-fragment was injected and hybridized on the surface, see FIG. 11. The figure also shows the result when a control consisting of a 207-base pair long single-stranded fragment from tyrosinase mRNA was used as sample. The selectivity is indeed very good.

EXAMPLE 8

An oligonucleotide probe comprising 8 nucleotides might bind, at least with some of the bases, to sequences which occur randomly in a mixed biological sample. Another probe consisting of 20 base-pairs (SEQ.ID.NO.2) was therefore immobilized on the measuring electrode in the same way as described above. The probe was towards the end of the cytomegalo virus fragment. FIG. 12 shows that a response indeed is obtained.

EXAMPLE 9

There might be some disadvantages with probes directed towards the end of a DNA fragment. It was found, however, that with a probe directed towards a middle section the capacitance change did indeed occur at first but the capacitance returned to the original value after some time in the flow. The probe was therefore immobilized so that it would lie flat on the measuring electrode surface.

34 $\mu$l of the oligonucleotide 25-mer (SEQ.ID.NO.3) was incubated on ice for 10 min. with 20 $\mu$l M NaHCO$_3$, pH 9.6, 2 $\mu$l 8 mM N-bromosuccinimide in water, and water to a final volume of 200 $\mu$l. Thereafter an electrode pretreated with cysteamine, as described above, was dipped in the solution and the reaction took place at 50° C. during 1 hour.

---

What is claimed is:

1. A capacity affinity sensor for determining the presence of and/or the quantity of a compound of interest in a liquid sample, comprising:
    a noble metal surface; and
    a first immobilized and electrically insulating layer having a first measurable capacitance, wherein the first immobilized and electrically insulating layer comprises a first self-assembled monolayer-forming compound having coupled thereto an affinity compound, and a second self-assembled monolayer-forming compound, the noble metal surface being at least 99% covered with the first immobilized and electrically insulating layer;
    wherein the affinity compound, upon contact with the liquid sample, is capable of specifically binding the compound of interest so as to form a second immobilized and electrically insulating layer having a second measurable capacitance.

2. The capacity affinity sensor of claim 1 wherein the noble metal is gold, silver, copper, platinum or palladium.

3. The capacity affinity sensor of claim 1 wherein the noble metal surface is provided by a piece of the noble metal.

4. The capacity affinity sensor of claim 3 wherein the piece of a noble metal is in the shape of a rod.

5. The capacity affinity sensor of claim 1 wherein the noble metal surface is provided as a layer of the noble metal coating a piece of an electrically insulating material.

6. The capacity affinity sensor of claim 5 wherein the electrically insulating material is glass or quartz.

7. The capacity affinity sensor of claim 1 wherein the first self-assembled monolayer-forming compound is D/L-thioctic acid, activated with 1-(3-dimethylaminopropyl)-3-ethyl-carbodiimide.

8. The capacity affinity sensor of claim 1 wherein the second self-assembled monolayer-forming compound is a thiol comprising 3–25 carbon atoms in a straight saturated chain.

9. The capacity affinity sensor of claim 8 wherein the thiol is 1-dodecanethiol.

10. The capacity affinity sensor of claim 1 wherein the affinity compound is an antibody, a monoclonal antibody, an antibody fragment or a F(ab')$_2$ fragment.

11. The capacity affinity sensor of claim 1 wherein the affinity compound is a nucleic acid.

12. The capacity affinity sensor of claim 1 wherein the affinity compound is a single-stranded DNA compound.

13. The capacity affinity sensor of claim 1 wherein the sensor is adapted to determine the presence of human chorionic gonadotripin hormone (HCG), interleukin-2, human serum albumin, atrazine, or a DNA sequence.

14. A method for qualitatively or quantitatively determining the presence of a compound of interest in a liquid sample, comprising the steps of:
    (a) contacting the sensor of claim 1 with a reference liquid not containing the compound of interest and determining the capacitance of the sensor;
    (b) contacting the sensor with a sample suspected of containing the compound of interest so as to bind the compound of interest and determining the capacitance of the sensor having the compound of interest bound thereto; and
    (c) calculating the difference between the capacitance measured in step (a) and the capacitance measured in step (b) and optionally calculating the amount of the compound of interest by using prerecorded calibration data.

15. The method of claim 14 wherein the compound of interest is human chorionic gonadotropin hormone (HCG), interleukin-2, human serum albumin, atrazine, or a DNA sequence.

16. A capacity affinity sensor for determining the presence of and/or the quantity of a compound of interest in a liquid sample, comprising:

a noble metal surface; and a first immobilized and electrically insulating layer having a first measurable capacitance, wherein the first immobilized and electrically insulating layer comprises a first self-assembled monolayer-forming compound and a second self-assembled monolayer-forming compound, the noble metal surface being at least 99% covered with the first immobilized and electrically insulating layer;

wherein upon contact with the liquid sample, the first self-assembled monolayer-forming compound is capable of specifically binding the compound of interest so as to form a second immobilized and electrically insulating layer having a second measurable capacitance.

17. A method for qualitatively or quantitatively determining the presence of a compound of interest in a liquid sample, comprising the steps of:

(a) contacting the sensor of claim 16 with a reference liquid not containing the compound of interest and determining the capacitance of the sensor;

(b) contacting the sensor with a sample suspected of containing the compound of interest so as to bind the compound of interest and determining the capacitance of the sensor having the compound of interest bound thereto; and (c) calculating the difference between the capacitance measured in step (a) and the capacitance measured in step (b) and optionally calculating the amount of the compound of interest by using prerecorded calibration data.

18. The method according to claim 17 wherein the compound of interest is human chorionic gonadotropin hormone (HCG), interleukin-2, human serum albumin, atrazine, or a DNA sequence.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 8 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

-continued

```
TTAGGAGA                                                                      8

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

TAGGGAAGGC TGAGTTCTTG                                                         20

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

TAGGGAAGGC TGAGTTCTTG GTAAA                                                   25
```